US008105532B2

(12) United States Patent
Harmon et al.

(10) Patent No.: US 8,105,532 B2
(45) Date of Patent: Jan. 31, 2012

(54) MOBILE DISINFECTANT DEVICE AND METHODS

(75) Inventors: Nicholas Harmon, Waitsfield, VT (US); Ryan Douglas, Stillwater, MN (US)

(73) Assignee: Verilux, Inc., Waitsfield, VT (US)

( * ) Notice: Subject to any disclaimer, the term of this patent is extended or adjusted under 35 U.S.C. 154(b) by 289 days.

(21) Appl. No.: 12/290,113

(22) Filed: Oct. 27, 2008

(65) Prior Publication Data
US 2010/0104471 A1    Apr. 29, 2010

(51) Int. Cl.
*A61L 2/10* (2006.01)
(52) U.S. Cl. .... 422/24; 422/186.3; 96/224; 250/455.11; 250/493.1
(58) Field of Classification Search ............ 422/24, 422/186.3; 96/224; 250/493.1, 455.11, 504 H
See application file for complete search history.

(56) References Cited

U.S. PATENT DOCUMENTS

| | | | |
|---|---|---|---|
| 2,632,912 A | 3/1953 | Cuddeback |
| 2,648,396 A | 8/1953 | Kirby |
| 2,681,467 A | 6/1954 | Guyer |
| 3,970,856 A | 7/1976 | Mahaffey et al. |
| 3,975,790 A | 8/1976 | Patterson |
| 4,907,316 A | 3/1990 | Kurz |
| 4,952,369 A | 8/1990 | Belilos |
| 5,233,283 A | 8/1993 | Kennedy |
| 5,259,380 A | 11/1993 | Mendes et al. |
| 5,420,768 A | 5/1995 | Kennedy |
| 5,500,009 A | 3/1996 | Mendes et al. |
| 5,634,711 A | 6/1997 | Kennedy et al. |
| 5,728,090 A | 3/1998 | Martin et al. |
| 5,783,909 A | 7/1998 | Hochstein |
| 5,920,075 A | 7/1999 | Whitehead |
| 5,968,455 A | 10/1999 | Brickley |
| 6,063,108 A | 5/2000 | Salansky et al. |
| 6,239,442 B1 | 5/2001 | Iimura |
| 6,242,753 B1 | 6/2001 | Sakurai |
| 6,283,956 B1 | 9/2001 | McDaniel |
| 6,443,978 B1 | 9/2002 | Zharov |
| 6,656,424 B1 | 12/2003 | Deal |
| 6,911,177 B2 | 6/2005 | Deal |
| 6,953,940 B2 | 10/2005 | Leighley et al. |
| 6,976,984 B2 | 12/2005 | Cense et al. |
| 7,173,254 B2 | 2/2007 | Sauska et al. |
| 7,175,806 B2 | 2/2007 | Deal et al. |
| 7,201,765 B2 | 4/2007 | McDaniel |

(Continued)

FOREIGN PATENT DOCUMENTS
WO    2005/011755 A2    2/2005

*Primary Examiner* — Sean E Conley
(74) *Attorney, Agent, or Firm* — Dardi & Herbert PLLC

(57) ABSTRACT

Ultraviolet light is an effective sterilization agent. Convenient mobile sterilization devices are described herein that, in certain embodiments, provide indications to a user of how much sterilizing light is required for a given sterilization goal and how much light has been applied to a surface towards that goal. Users can move the devices across a target surface as needed to sterilize or disinfect the surface, with the device tracking the dosage applied to the surface. One embodiment of a mobile device that comprises an ultraviolet C (UVC) light source, a distance detector, an indicator, and a microprocessor that receives data from the distance detector for calculating an intensity of the light from the source on a target surface and for calculating a dosage of the light on the surface to provide a signal to the indicator when a predetermined dosage is achieved.

31 Claims, 11 Drawing Sheets

U.S. PATENT DOCUMENTS

| | | |
|---|---|---|
| 7,211,813 B2 * | 5/2007 | Jensen .................. 250/504 H |
| 7,444,711 B2 | 11/2008 | Garcia et al. |
| 7,581,283 B2 | 9/2009 | Yoo et al. |
| 7,610,652 B2 | 11/2009 | Seo et al. |
| 2004/0244138 A1 | 12/2004 | Taylor et al. |
| 2005/0000543 A1 * | 1/2005 | Taylor et al. .................. 134/18 |
| 2005/0022844 A1 | 2/2005 | Field et al. |
| 2005/0055070 A1 | 3/2005 | Jones et al. |
| 2005/0065579 A1 | 3/2005 | Chen et al. |
| 2005/0091785 A1 | 5/2005 | Yuen |
| 2005/0149150 A1 | 7/2005 | McDaniel |
| 2005/0228463 A1 | 10/2005 | Mac et al. |
| 2005/0234383 A1 | 10/2005 | Dougal |
| 2005/0261750 A1 | 11/2005 | McDaniel |
| 2006/0185116 A1 | 8/2006 | Lee et al. |
| 2006/0185117 A1 | 8/2006 | Seo et al. |
| 2006/0236496 A1 | 10/2006 | Oh et al. |
| 2006/0278088 A1 | 12/2006 | Helsel |
| 2006/0293727 A1 | 12/2006 | Spooner et al. |
| 2007/0023710 A1 | 2/2007 | Tom et al. |
| 2007/0032843 A1 | 2/2007 | Hsu |
| 2007/0067943 A1 | 3/2007 | Makarov |
| 2007/0129778 A1 | 6/2007 | Dougal |
| 2007/0167999 A1 | 7/2007 | Breden et al. |
| 2007/0185553 A1 | 8/2007 | Kennedy |
| 2007/0192986 A1 | 8/2007 | Garcia et al. |
| 2007/0209143 A1 | 9/2007 | Choi et al. |
| 2007/0209144 A1 | 9/2007 | Fester et al. |
| 2007/0231193 A1 | 10/2007 | Jung et al. |
| 2008/0004611 A1 | 1/2008 | Houbolt et al. |
| 2008/0052872 A1 | 3/2008 | Cho |
| 2008/0103563 A1 | 5/2008 | Powell et al. |
| 2008/0140164 A1 | 6/2008 | Oberreiter et al. |
| 2008/0256741 A1 | 10/2008 | Garcia et al. |
| 2008/0260601 A1 | 10/2008 | Lyon |
| 2008/0294227 A1 | 11/2008 | Perez |
| 2009/0126145 A1 | 5/2009 | D'Agostino et al. |
| 2009/0183335 A1 | 7/2009 | Griffith et al. |
| 2009/0205664 A1 | 8/2009 | Lyon |
| 2009/0240310 A1 | 9/2009 | Kennedy |

* cited by examiner ured the source towards that goal. Users can move the devices across a target surface as needed to sterilize or disinfect the surface, with the device tracking the dosage applied to the surface.

MOBILE DISINFECTANT DEVICE AND METHODS

TECHNICAL FIELD

The technical field relates to mobile devices for ultraviolet light disinfection.

BACKGROUND

Ultraviolet light is an effective sterilization agent. The ultraviolet light breaks down living organisms to render them harmless.

SUMMARY

Convenient mobile sterilization devices are described herein that, in certain embodiments, provide indications to a user of how much sterilizing light is required for a given sterilization goal and how much light has been applied to a surface towards that goal. Users can move the devices across a target surface as needed to sterilize or disinfect the surface, with the device tracking the dosage applied to the surface.

One embodiment of a mobile device that comprises an ultraviolet C (UVC) light source or other ultraviolet light source, a distance detector, an indicator, and a microprocessor that receives data from the distance detector for calculating an intensity of the light from the source on a target surface and for calculating a dosage of the light on the surface to provide a signal to the indicator when a predetermined dosage is achieved. The device may be equipped with one or more of: a movement sensor that provides device movement data to the microprocessor to include in the calculation of the dosage; a wheel for rolling the device across the surface; a light or an audio signal indicator, a display, a display that depicts subareas of the target area and the dosage applied to the subarea; an xy accelerometer, an xyz accelerometer, an accelerometer that provides acceleration data to the microprocessor to be incorporated into the calculation of the dosage; a movement sensor that provides an acceleration in an x-direction and an acceleration in a y-direction, with the target area having xy coordinates; or a microprocessor configured to calculate the exposure with an intensity of the light source at the surface, a predetermined value of intensity of the light source at the light source, and a distance from the light source to the surface. Some embodiments of the device are hand-held and movable over the surface by a user grasping a portion of the device. The target area may be represented as having an x-direction and a y-direction, with the calculations subdividing the area into subareas and calculating a dosage for each grid member. A display may provide a visual representation of a dosage received at each grid member. The device may have executable programming or hardware for predetermined sterilization dosages for one of more organisms or conditions in the group consisting of typhoid, influenza, hepatitis, anthrax, mold A, and mold B and/or programming for predetermined sterilization dosages from about 6,000 to about 44,000 microwatts per square centimeter.

Some embodiments are methods of disinfecting. For instance, a method of disinfecting comprising providing an ultraviolet light source, a distance detector, an indicator, and a microprocessor that receives data from the distance detector for calculating an intensity of the light from the source on a target surface and for calculating a dosage of the light on the surface to provide a signal to the indicator when a predetermined dosage is achieved, with the device comprising a movement sensor that provides device movement data to the microprocessor to include in the calculation of the dosage, and moving the device to expose the target area to the light source until the indicator indicates the predetermined dosage is achieved. The indicator may comprise a display that depicts subareas of the target area and the dosage applied to the subarea, wherein the user moves the device over the subareas until each subarea has achieved the predetermined dosage. The movement sensor may comprise an accelerometer (e.g., xy or xyz) that provides acceleration data to the microprocessor to be incorporated into the calculation of the dosage. The movement sensor may provide an acceleration in an x-direction and an acceleration in a y-direction, with the target area having xy coordinates. Other coordinates may be used, e.g., radial, spherical. The target area may be represented as having an x-direction and a y-direction, with the calculations subdividing the area into subareas and calculating a dosage for each grid member.

Some embodiments relate to processes of making a mobile disinfecting device. One embodiment is a method of making a mobile disinfecting device for sanitizing or sterilizing a surface comprising mounting an ultraviolet light source in a housing in electronic communication with a microprocessor that communicates with a movement sensor and a distance detector, wherein the movement sensor is configured to provide movement information to the microprocessor for a calculation of an exposure of the surface to the light source, for a calculation of a dosage at the surface, and for activation of an indicator when the dosage achieves a predetermined exposure. The device may have features as described above or elsewhere herein.

DETAILED DESCRIPTION OF PREFERRED EMBODIMENTS

Figure 1A:
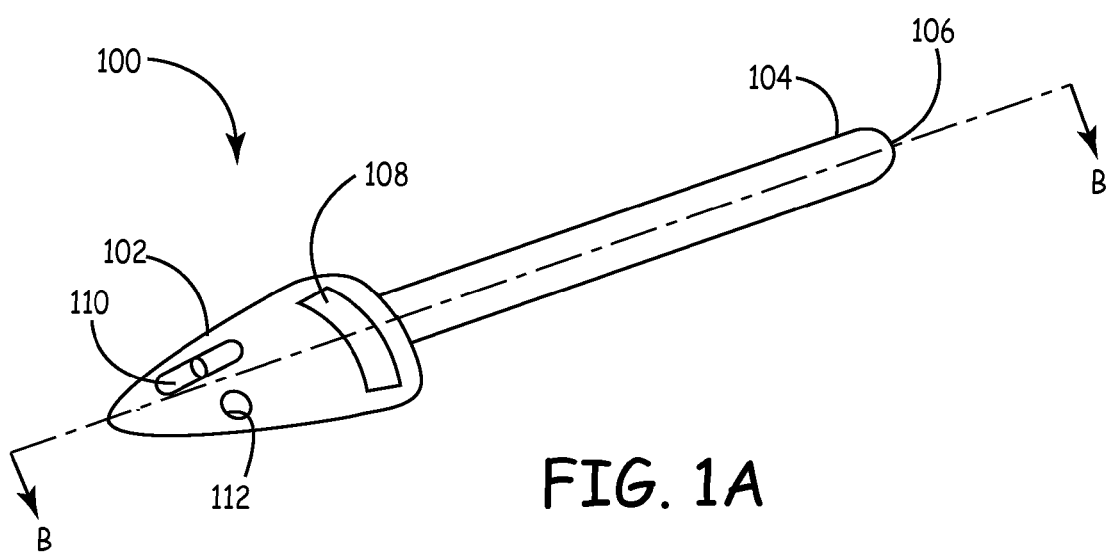
FIG. 1A is a perspective view of a disinfecting hand-held wand embodiment.
Figure 1B:
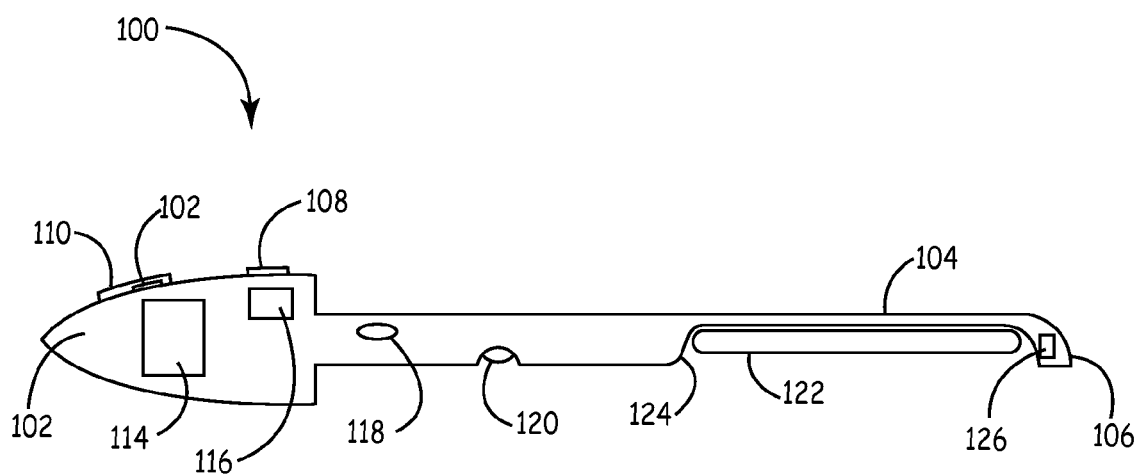
FIG. 1B is a cross-sectional view along line B-B of FIG. 1A.

FIG. 1 depicts a perspective view of an embodiment of the invention, with hand-held wand 100 having a proximate portion 102 graspable by a user, a distal portion 104 with distal tip 106, a display 108, switch 110 with optional plurality of settings, and cycle button 112. In cross-section along line B-B, device 100 has battery 114, microprocessor 116, accelerometer 118, distance detector 120, targeting light source 122 received in light source cavity 124, and facing detector 126.

Figure 2:
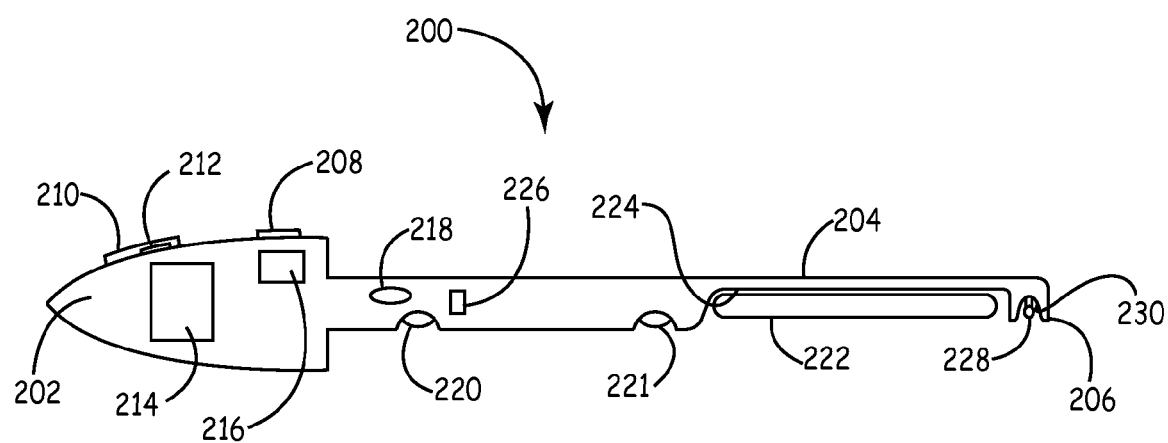
FIG. 2 is a cross-sectional view of an alternative embodiment of a hand-held wand embodiment.

FIG. 2 is a cross-sectional view of an alternative embodiment of the device of FIG. 1, with hand-held wand 200 having a proximate portion 202 graspable by a user, a distal portion 204 with distal tip 206, a display 208, switch 210 with optional plurality of settings, and cycle button 212. Device 200 has battery 214, microprocessor 216, accelerometer 218, distance detectors 220, 221, light source 222 received in light source cavity 224, and facing detector 226. A light 228 in light cavity 230 is also provided.

Figure 3A:
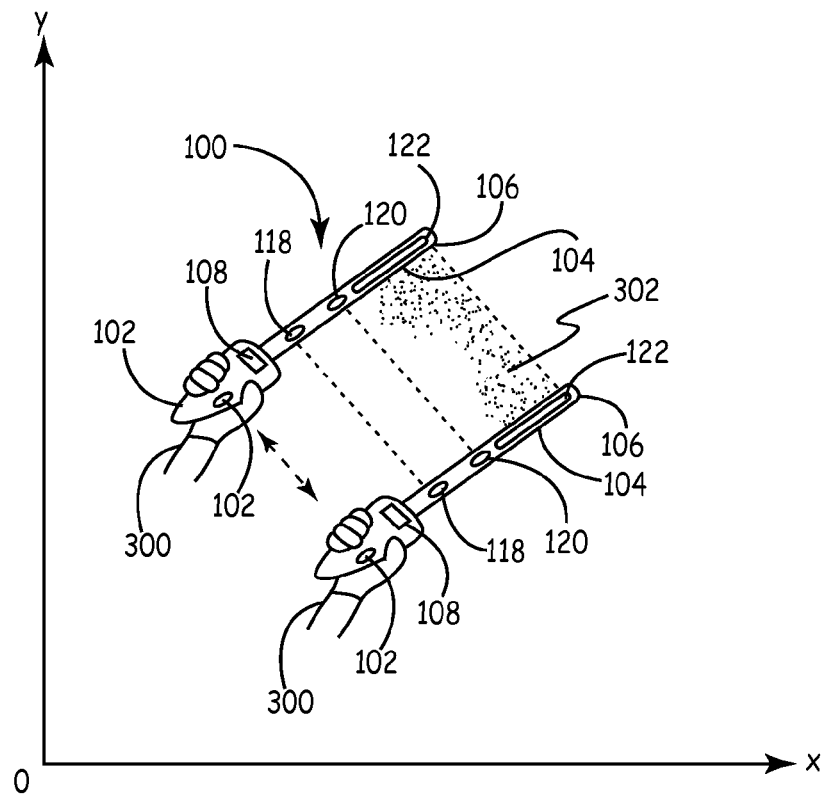
FIG. 3A is a top view of a hand-held wand in use.
Figure 3B:
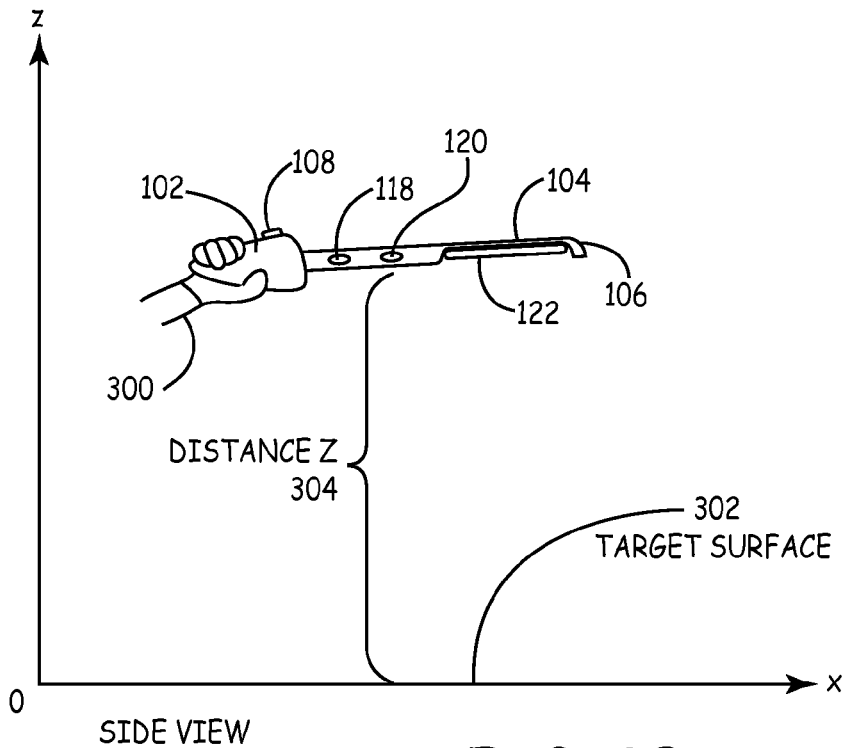
FIG. 3B is a side view of the use of FIG. 3A.

FIG. 3 depicts device 100 in use, with the device depicted schematically in partial detail for purposes of illustration, with positions of light source 122 and accelerometer 118 being indicated. User 300 grasps device 100 by proximate portion 102 and holds it over target surface 302. An xyz coordinate system is used herein as a frame of reference with xy referring to a plane of the target surface and the z-coordinate indicating perpendicular distance from the surface plane. Thus a user sterilizing a target area on a floor would typically stand on the xy plane of the floor an hold a wand a certain z-distance from the floor. User 300 turns on device 100 and optionally selects a setting with switch 110, presses cycle button 112, and moves device 100 over target area 302 with light source 222 directed towards the target area until an indicator on display 108 provides an indication that a predetermined dosage of light from light source 122 has been provided to target area 302. Device 200 may be used similarly, with targeting light source 228 providing illumination to project targeting light or a targeting light pattern on surface 302 for the user's reference.

Figure 4:
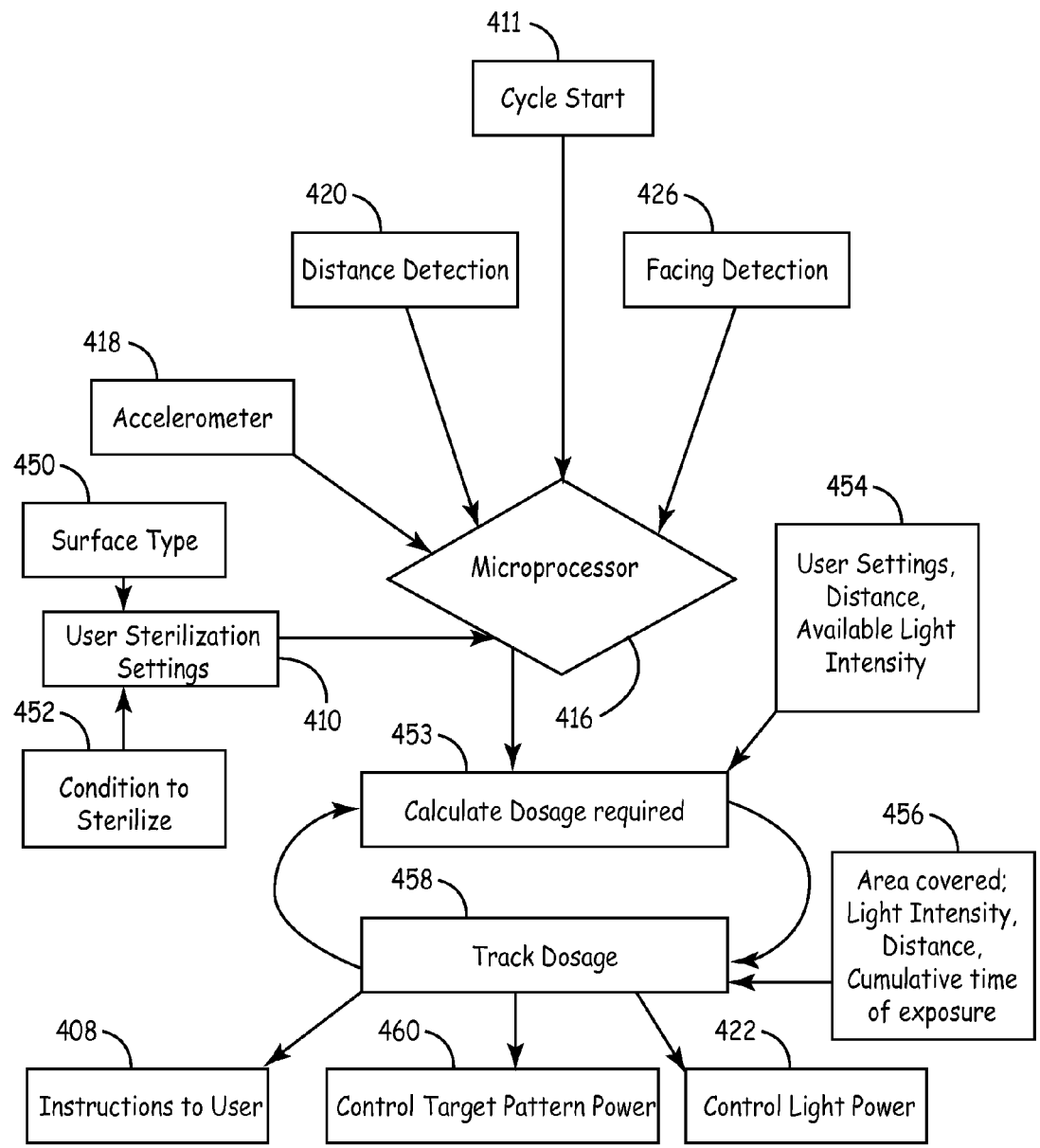
FIG. 4 is a schematic of controllers and output for a mobile disinfecting device.
Figure 5A:
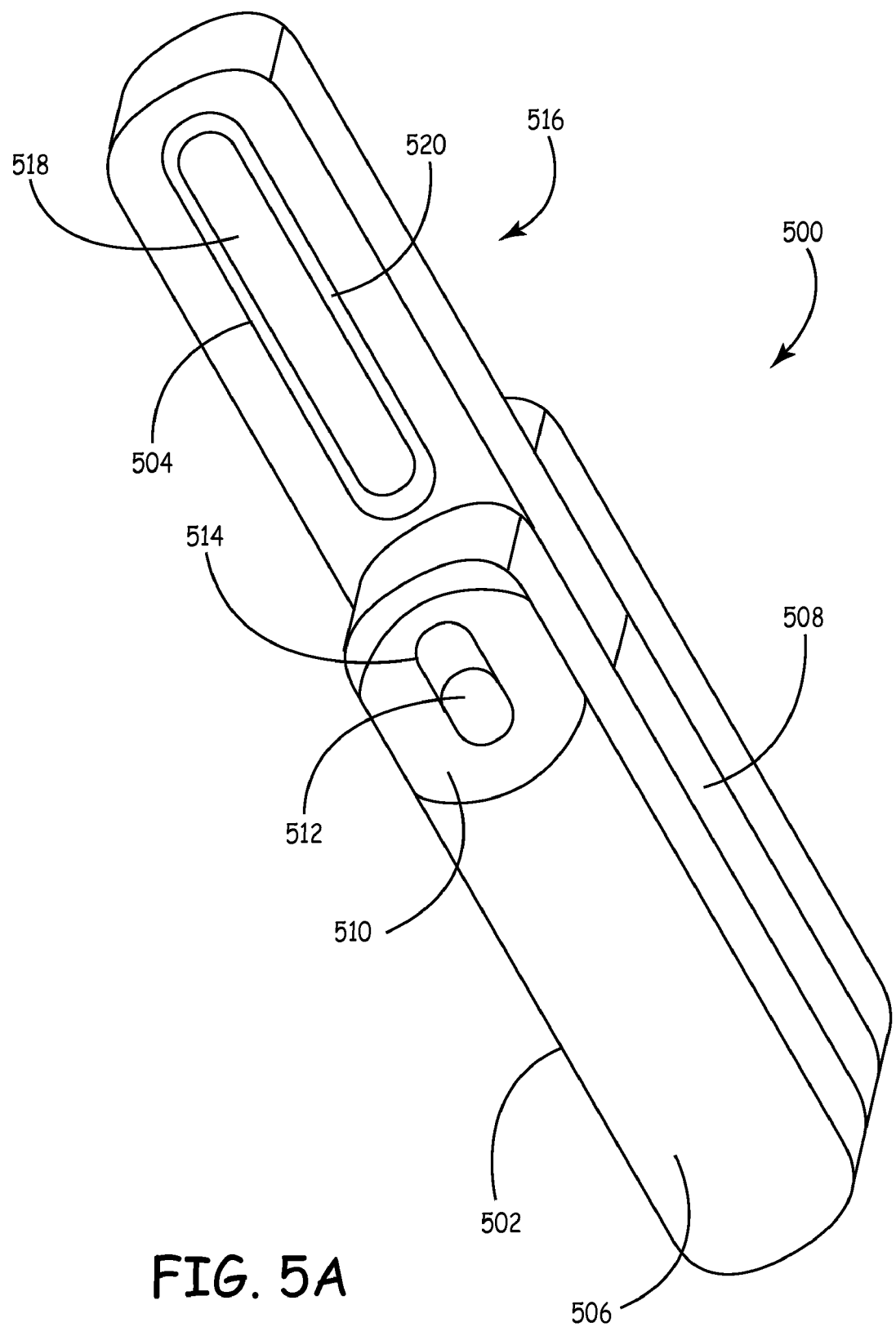
FIG. 5A is a perspective view of a disinfecting hand-held wand embodiment in an extended in-use position.
Figure 5B:
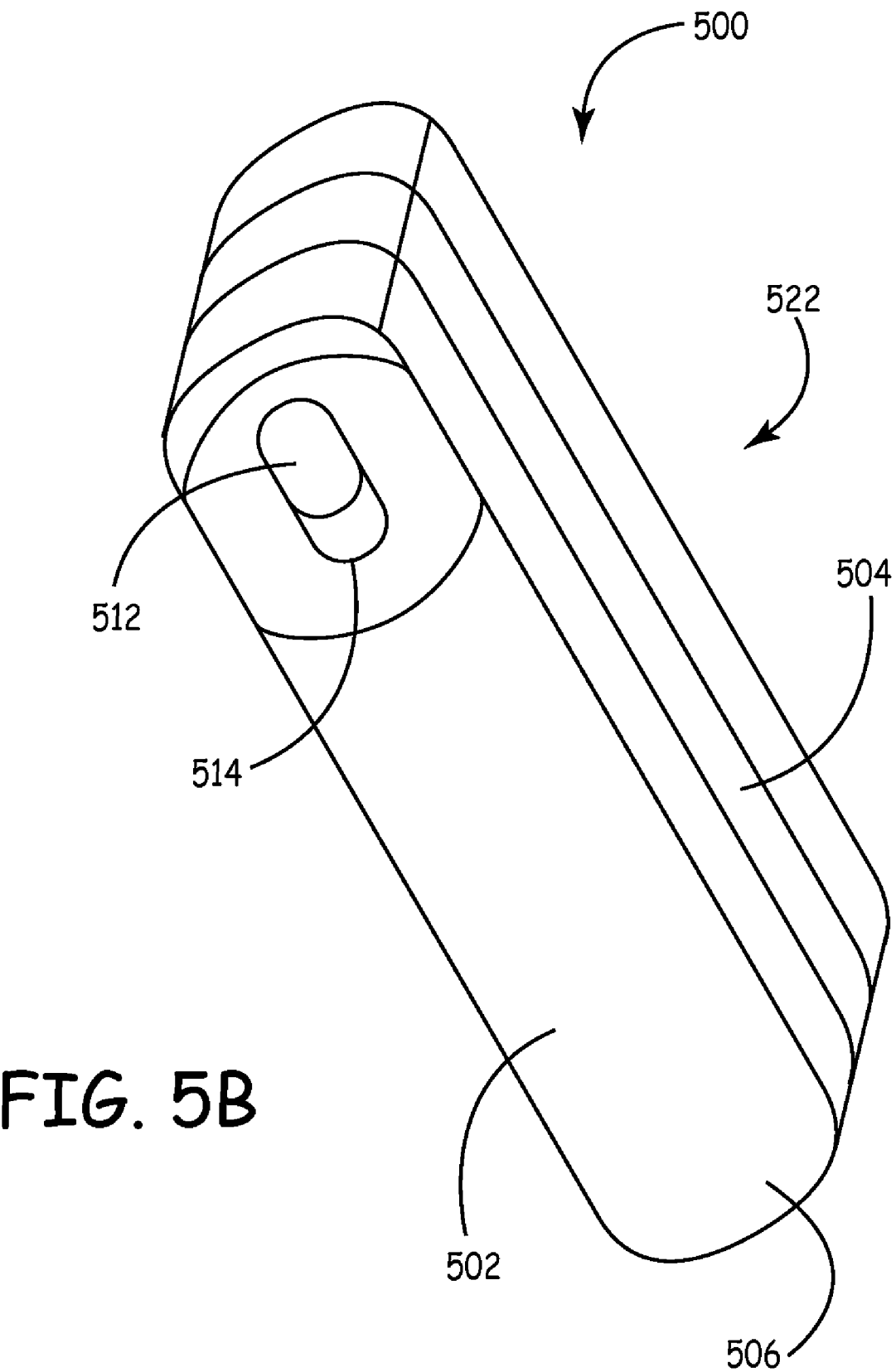
FIG. 5B is a perspective view of the embodiment of FIG. 5A in a storage position.
Figure 5C:
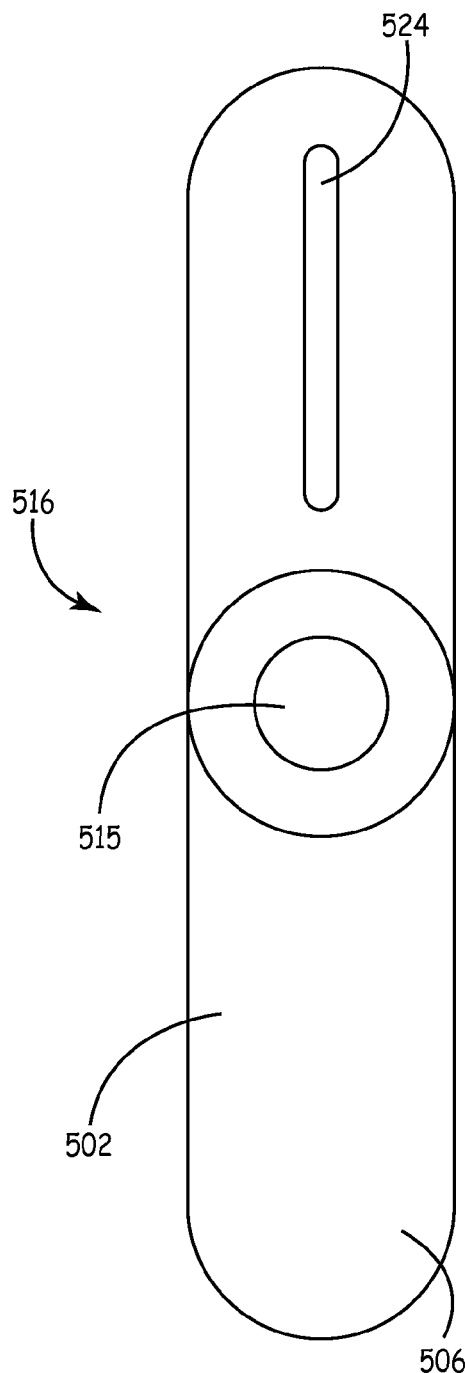
FIG. 5C is a top view of the embodiment of FIG. 5A.
Figure 5D:
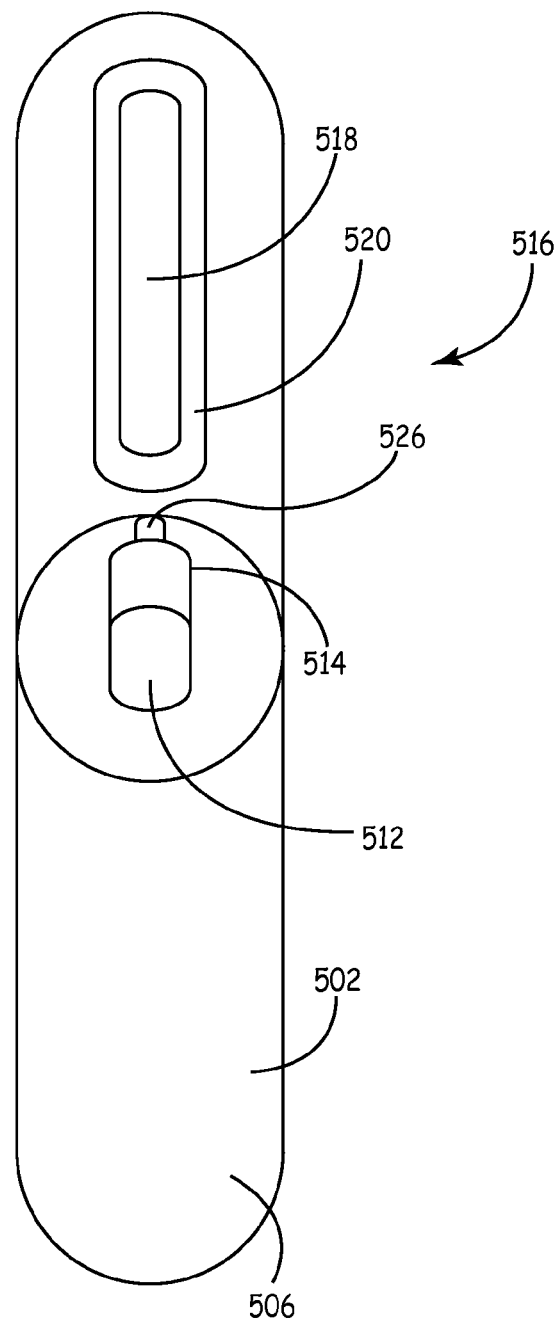
FIG. 5D is bottom view of the embodiment of FIG. 5A.

FIG. 4 is a block diagram depicting an embodiment for interconnection of components of FIGS. 1-3 or other devices, and is described in terms of the embodiment of FIG. 2. Block diagram conceptually shows processing by microprocessor 216 in block 416, instructions to user 408 for display 208, settings control 410 from switch 210 for determining one of a plurality of settings, cycle start 411 from cycle button 212, accelerometer input 418 from accelerometer 218, distance detector input 420 from distance detector 220, light source control 422 to control light source 222 and facing detector input 426 from facing detector 226. Exemplary input options 450, 452 through setting control 410 are surface type and condition to sterilize, respectively. Microprocessing as at 416 calculates as at 453 a required dosage based on required dosage factors 454 such as preset criteria including light source intensity and dosage needed to achieve the sterilization settings 410 and real-time data such as distance 304. Upon cycle initiation by user 300 as at 408, microprocessing 416 tracks inputs to calculate a dosage of target surface 302. Dosage tracking as at 458 uses inputs 456 that may include preset criteria including light source area, focus, and intensity of light source 222 as modified in a known manner by other settings, and real-time data such as distance 304 and the portion of area covered for the target area 302. Microprocessing outputs may include control of targeting light as at 460.

A dosage of all or portions of the target area may be tracked in essentially real time by a microprocessor using inputs including accelerometer inputs. Accelerometers, e.g., 118, 218 provide acceleration data. An xyz accelerometer may be used to provide an object's attitude, i.e., its coordinates in an xyz coordinate system. In the case of a known geometry, all the points on the object can be mapped into the xyz coordinate position with a single xyz accelerometer. Alternatively, separate devices can provide inputs that in combination describe an object's attitude, for instance an xy accelerometer and a tilt indicator for the z-position. A timer in the microprocessor or separately provided can be used to track coverage in real time or pseudotime. When a cycle is initiated, or upon other trigger to begin tracking, the time spent a location can be recorded and accumulated to a record that tracks the amount of time a surface has been exposed to a light source. Distance information, e.g., as at 304, can be used with light source intensity information to calculate how much light has been received at a coordinate. Various methods of tracking the dosage may be used according to the inputs and dosage model parameters. One method imposes an imaginary grid on the surface that is exposed to the light source and accumulates the time and intensity of light projected onto each grid member. The size of grid members can be increased or decreased as desired for accuracy or computational ease. Alternatively, other types of subareas may be used instead of grid blocks.

In general, the device may be provided with instructions that outline usage guidelines. In one method, the user is instructed to provide a series of passes over the intended target area to define the target area's size for calculation purposes. The area is then subdivided and dosage for each area is calculated as the user treats the areas. When all or some proportion of the areas accumulate a dosage that meets or exceeds a desired dosage, the microprocessor provides a signal to a display to indicate to the user that the cycle is complete.

FIG. 5 depicts an alternative hand-held wand embodiment. Device 500 has a housing with body 502 and retractable member 504. Body 502 has proximate portion 506, storage slot 508 for member 504, and pivoting assembly 510. Pivoting assembly has biased tab 512, tab slot 514, and a pin member 515 for pivotal movement of member 504 in and out of storage slot 508. In the storage position, the light source is protected inside the device and no part of it is exposed to potential damage. In this embodiment, the retractable member is completely folded into the body, meaning that its top and bottom are within the slot, with only a side being exposed. A user may press tab 512 to displace it from tab slot 514 so that the pivotal movement may be accomplished; when tab 512 is in tab slot 514, member 504 is locked in an extended position 516. Sterilizing light source 518 is housed in light source receptacle 520. FIG. 5B depicts device 500 in a storage position 522 with member 504 received by storage slot 508. Biased tab 512 is in slot 514 to lock device 500 in the storage position. A user may depress tab 512 out of slot 514 to move member 504 and 502 relative to each other. Window 524 may optionally be provided to allow filtered light from light source 518 to pass through to the user, with the filtering removing any harmful wavelengths. Alternatively window 524 may be replaced with some indicator of a position of the light source on the opposing side of the device, e.g., a decal, a printed indicium, or a raised portion of the housing. Biased position indicator 526 may be used to indicate to a microprocessor (not shown) that the device is in a storage position or extended position, e.g., the indicator is forced downwards to make a contact when in the extended position but otherwise makes no contact to prevent operation of the light source. Device 500 may have components as described with respect to FIGS. 1-4 above, or other components described herein; in use, device 500 may be used in a manner similar to these other devices. The hand-held sterilization devices in U.S. Pat. No. 7,834,335 which is hereby incorporated by reference herein, may also be adapted for use as described herein, e.g., with a distance detector and microprocessing functions.

Figure 6A:
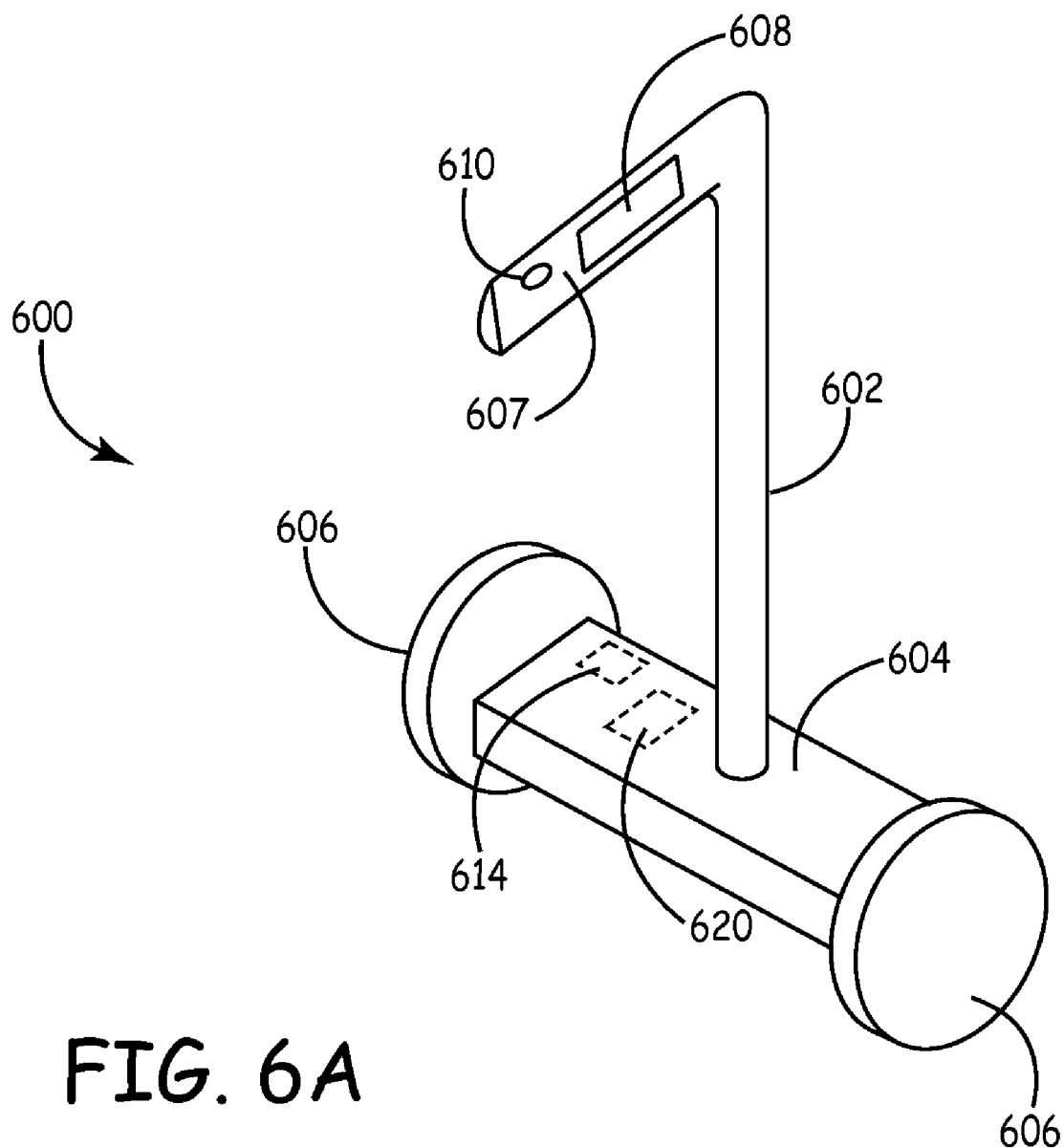
FIG. 6A is a perspective view of a mobile rollable disinfecting unit.
Figure 6B:
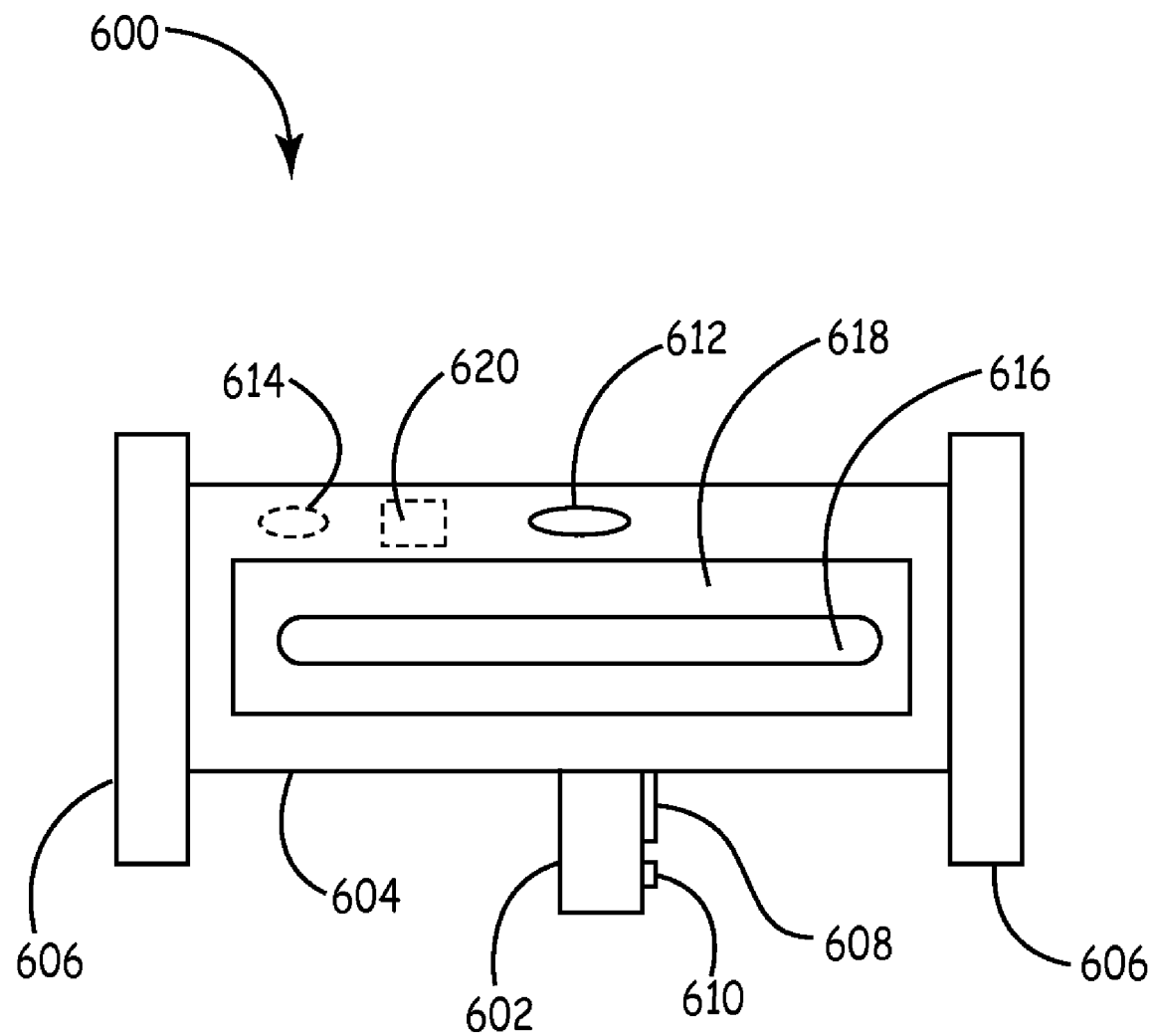
FIG. 6B is a bottom view of the embodiment of FIG. 6A.

FIG. 6 depicts an alternative device that is mobile but not hand-held. Mobile refers to a device that moves to pass the sterilizing light source over the target area and is in contrast to a static device that sterilizes without direct movement. Accordingly, a device that is left in a room to sterilize the room without being moved is static. A hand-held device that a human user moves during a cycle is mobile, as is a robot equipped to move about an area, as in the popularly known IROBOT series of robotic floor vacuum cleaners. A device that receives a component for sterilization into an enclosed chamber is static. Rollable sterilizer 600 has handle 602 attached to base 604 that is attached to wheels 606. Handle 602 has proximal portion 607 for gripping by a user, display 608 for display to the user, and cycle start button 610. Base 604 has distance detector 612, accelerometer 614, sterilizing light source 616 in receptacle 618, and microprocessor 620. In use, a user grips portion 607, actuates cycle start button 610, and rolls device 600 across a target area. As already described for other mobile devices, the target area may be sterilized or sanitized by passing the light source over the target area, with the display signaling to the user as needed and with the microprocessor coordinating inputs to track and report progress in the overall process. The microprocessor and accelerometer may be positioned outside of the base or in the base as depicted. The distance may be assumed to be fixed for calculation purposes since the wheels hold the light source a fixed distance from the target surface, in which case the distance detector may optionally be eliminated or used merely as a safety device to turn off the light source when a surface is not detected within a preset distance.

Alternatively, a vacuum cleaner may be equipped with an ultraviolet light source, a distance detector, an indicator, and/ or a microprocessor that receives data from the distance detector for calculating an intensity of the light from the source on a target surface and for calculating a dosage of the light on the surface to provide a signal to the indicator when a predetermined dosage is achieved. The light source may be mounted according to the style of vacuum cleaner to illuminate the surface being vacuumed, e.g., canister or upright, see for example U.S. Pat. No. 2,632,912, U.S. Pat. No. 4,907,316, US 2006-0185116, US 2007-0192986 each of which are hereby incorporated by reference herein to the extent they do not contradict what is explicitly disclosed herein. The other features and options described herein may further be incorporated into such a device.

Hand-held wand is a term referring to a device for a user to hold and support the entire device in a hand and move across a target area. Embodiments of hand-held devices include those with a weight of less than about 10 lbs, less than about 5 lbs, less than about 1 lb and less than about 8 ounces; artisans will immediately appreciate that all the ranges and values within the explicitly stated ranges are contemplated. A switch or a button that is actuated by a user is a broad term and may include, for example, a toggle, a sliding switch that allows adjustable control of the component being switched, hand-actuation, foot actuation, knobs, rheostats, and wheels (e.g., thumbwheel). Batteries may be disposable or rechargeable, e.g., by electric current or solar cells. A power cord and plug may be used to augment or substitute for battery-operation.

Figure 7:
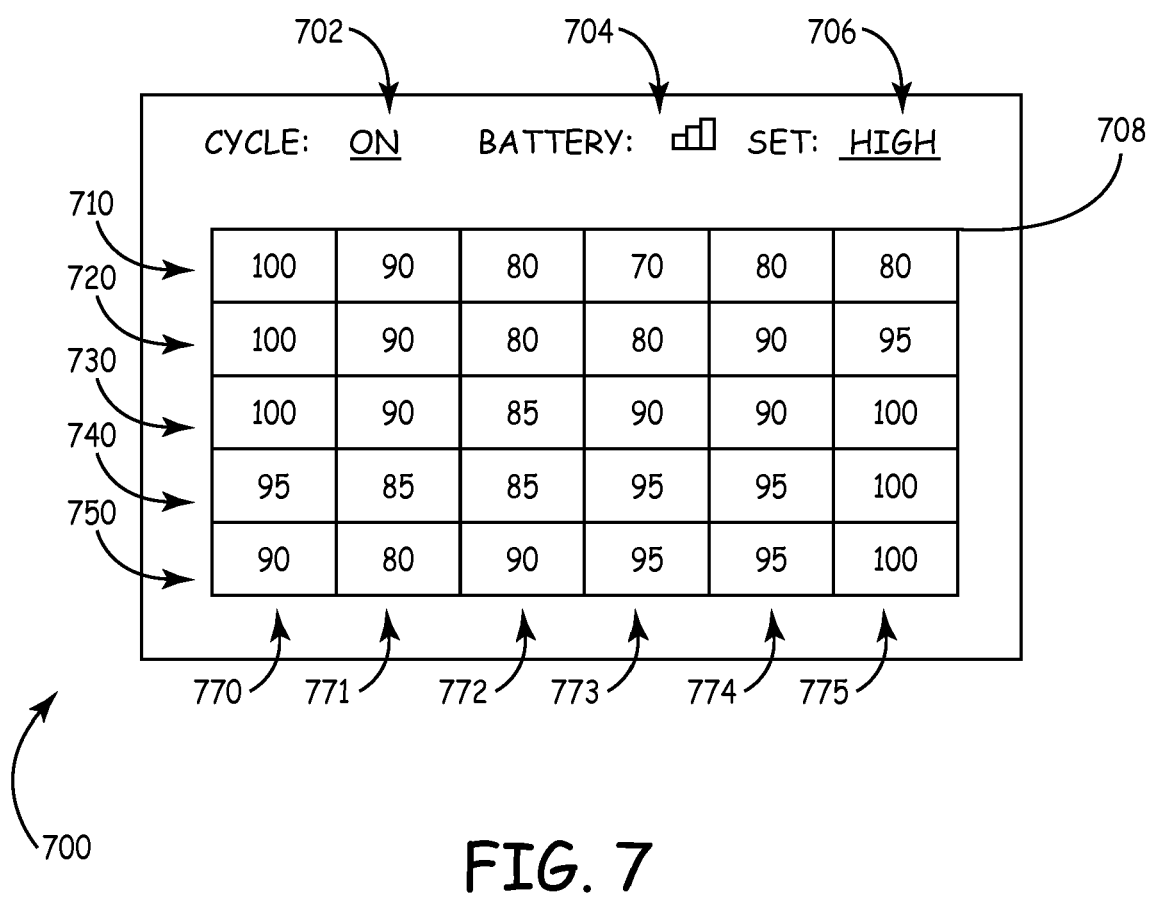
FIG. 7 illustrates a display for a disinfecting devices representing a target area as a plurality of subareas.

The term display is broad and includes, e.g., lights, light arrays, liquid crystal displays, and video displays. In general a display may be augmented with, or replaced by, audio signals, depending on the overall functionality of the display. In some embodiments, the display provides an indication that the target area has been treated and signals completion to the user. In other embodiments, the display further provides a graphical indication of what portions of the target area have been treated or require further treatment, as in FIG. 7, showing display 700 with cycle indicator 702, battery indicator 704, setting indicator 706, and area indicator 708 that is a virtual representation of target area 302 subdivided into a grid patter with rows 710, 720, 730, 740, 750, and columns 770 to 775. In use, the microprocessor provides data to the display to indicate a percentage completion of each grid member, e.g., block 770, 710 is depicted as 100% complete, with block 774, 720 being 90 percent complete. A user may iteratively view the display and adjust how the target area is swept to bring each grid area to a complete dosage of the source light. In the case of non-rectangular target areas, some of the blocks may be nonresponsive or otherwise indicated to be inactive, e.g., blacked out. Other indicia of completion may be used instead of percentages, e.g., colors to indicate levels of completion or levels of incompletion. In the case of a liquid crystal display, the grid may be represented graphically; in the case of an array of LED lights, the lights may be laid out to represent the grid and change color or state (e.g., steady, off, blinking, fast blink). In combination with a display, one embodiment involves initiating a cycle with a first step of mapping out a surface, with the user moving the mobile device over a target and optionally viewing the display to observe that the target area is mapped into the device, e.g., by observing the grid filled-in. After a cue from the device or from the user to the device (as by pressing the cycle button a second time, or a different button), the sterilization/sanitization cycle is initiated. In some embodiments, the distance detector is used to map contours of the target area, e.g., as in the metes and bounds of a pillow on an approximately flat surface being mapped by its height relative to the surface; optionally, the device may have a setting for contour-mapping, for mapping without distance detect input, or a combination of distance detection and xy area.

Accelerometers are useful for providing movement data to the microprocessor. An xy accelerometer, for instance, can provide xy movement data, with an acceleration of zero indicating a change in direction. An xyz accelerometer provides xyz movement data. In general, a distance detector may be used to provide z distance data in combination with an xy accelerometer to generate xyz movement data, or a single xyz accelerometer may be used. Some embodiments may use a plurality of z detectors to improve accuracy of the calculations, e.g., a plurality of distance detectors, or a distance detector and an xyz accelerometer. Some embodiments use a tilt detector as part of a calculation to determine the attitude of the device, with the device's attitude affecting dosage calculations since the distance from the target surface can affect the intensity of light received at the surface. Accordingly, some embodiments include an xy accelerometer and a tilt detector, and other embodiments may also include a tilt detector. An embodiment of a tilt detector is an electronic inclinometer, e.g., of a type in the group accelerometer, liquid capacitive, electrolytic, gas bubble in liquid, pendulum, and MEMS (Micro-Electro-Mechanical Systems).

Gyroscopes may also be used to measure orientation information. Gyroscopes include electronic gyroscopes and micro-electro-mechanical system (MEM) gyroscopes, e.g., as made by Systron Donner Inertial. In one embodiment, two gyroscopes are used with their axles at right angles to each another on a platform inside a set of gimbals; sensors on the gimbals' axles detect when the platform rotates. These signals may be processed, e.g., by microprocessor, to indicate the device's rotations relative to the platform. Further, an accelerometer may be used in combination with the pair of perpendicularly mounted gyroscopes to provide a measurement of the device's direction and how its motion is changing in all three directions. The pair of gyroscopes may alternatively be mounted so that the axis of rotation of the first and second gyroscopes are not parallel, i.e., are not necessarily perpendicular. Accordingly, an embodiment of the invention is a hand-held device that includes a first rotational sensor for determining rotation of the device about a first axis and generating a first rotational output associated therewith, a second rotational sensor for determining rotation of the pointing device about a second axis and generating a second rotational output associated therewith, an accelerometer for determining an acceleration of the pointing device and outputting an acceleration output associated therewith and a processing unit for receiving the first and second rotational outputs and the acceleration output. These data may be processed as described herein to track the movement of the device and dosages of light applied to a surface. In another embodiment, one gyroscope is used, with an accelerometer used to provide movement and positioning data along an axis that is not sensed by the rotational sensor.

Devices may include a wheel for providing distance data. Turning of the wheel indicates traverse according to the direction of the wheel's rotation, with other movement sensors providing data related to, e.g., pivots, turns or circles made by the user.

A facing detector may optionally be used. The facing detector can indicate if the device is pointing in a direction that is undesired such that the device or the light source may be turned off. In some embodiments, the light source or device is turned off when a facing detector is more than a predetermined value from vertical, with the value being in a range from, e.g., about 5 to about 90 degrees; in other words, the light is on if it points vertically down at the surface but is turned off when it deviates too much, e.g., is turned 30 degrees away; artisans will immediately appreciate that all the ranges and values within the explicitly stated ranges are contemplated, e.g., about 5, about 10, about 15, or about 20 degrees. For instance, a tilt switch may be used, e.g., switch equipped with an internal ball that is activated when a predetermined tilt angle has been achieved. In some embodiments, a distance detector is used as a safety device, with the light source being turned off if the distance is more than a predetermined value, e.g., from about 0.5 feet to about 10 feet; artisans will immediately appreciate that all the ranges and values within the explicitly stated ranges are contemplated.

Distance detectors include, for example, infrared or other light-based distance detectors. In general, a distance detect light source (e.g., infrared LED) emits light that is reflected at least partially by a surface; a detector mounted neat the emitter measures the amount of light received, with the emitter typically having a sensitivity matched to the emitted light wavelength. Photodiodes or CCD chips are available as detectors, with triangulation routines being available for enhanced distance calculation. Other distance detectors based on ultrasound may also be used, for example. A distance detector returns information that provides a distance. In contrast, a sensor that merely provides information about whether or the sensor is proximate to an object is a proximity sensor.

Certain embodiments provide for a target pattern or target light spot. Such indicia indicate to a user where the device is pointed. A light source, e.g., an LED or light bulb, can be activated to focus light in the direction that the sterilizing light source is pointed. A target pattern showing dark portions or light portions may be used, e.g., cross-hairs that appear as light or shadow on the target surface area. A pattern placed over such a source may be used to generate the target pattern.

Microprocessors may be used as needed to achieve the indicated calculations and processing. In general, a microprocessor refers to one or more computing devices that compute using hardware, software or firmware. A single microprocessor may be used in many embodiments, or a plurality of microprocessors may share computing tasks. The microprocessor may contain, or cooperate with, a computer-readable medium that provides computer-readable instructions, data, and electronic records. The term computing device is broad and includes microprocessors and integrated circuits that perform logical computing operations. Accordingly, for example, embodiments include computer readable media that have dosage records, tables of predetermined values, tables of predetermined dosages for comparing to actual dosage records, executable code for comparing values or providing a signal to a component after performing a logical operation based on real time or pseudotime input.

The light source may be an ultraviolet light (UV) source, e.g., ultraviolet A (UVA; about 400 nm to about 315 nm), ultraviolet B (UVB; about 315 nm to about 290 nm), ultraviolet C (UVC; about 290 nm to about 100 nm). UVC can be found in artificial sources such as mercury arc lamps and germicidal lamps. Light sources commonly referred to as UVC lamps can be used, e.g., as in the VERILUX TRAVEL WAND, which is a commercially available sterilization wand. Some light sources are referred to as high pressure UVC lamps, and typically have a peak at 254 nm and a secondary peak at about 185 nm. Medium pressure UVC lamps vary somewhat and typically have multiple peaks from abort 225 nm to about 600 nm.

Another light source embodiment is a mixture of UVA, and/or UVB, and/or UVC light in the range of about 185 nm to about 365 nm. The light may come from a filtered broad spectrum light source to provide a spectrum of light within the 185-365 range, or a plurality of light sources may be used that each provide at least one peak within the 185-365 range. For instance, two or three LED light sources may be used. Moreover, the light source may exclude wavelengths outside of the 185-365 range.

Table 1 details some dosages for sterilization. The cleaning mechanism of UV is a photochemical process. The indicated organisms or other compounds undergo breakdown when exposed to high intensity UV at about 240 to 290 nm. Shortwave ultraviolet light can destroy DNA in living microorganisms and breakdown organic material found in indoor air. UVC's effectiveness is directly related to intensity and exposure time. UV rays strike contaminants directly to penetrate it and break down its molecular bonds. This bond breakage translates into cellular or genetic damage.

Some embodiments accordingly relate to exposing a target area to a light source to sterilize the area for a particular condition or organism causing the condition until the target area is exposed to at least a dose of light that sterilizes the surface, meaning a 99.9% kill rate as measured under controlled conditions. Some embodiments relate to overexposing exposing a target area to a dosage that exceeds sterilization requirements, e.g., about 105 to about 1000% of the sterilization dosage; artisans will immediately appreciate that all the ranges and values within the explicitly stated ranges are contemplated, e.g., from about 110% to about 200%. Such overexposure can be used to compensate for less than ideal conditions such as irregularities or impurities in the target area. Other embodiments relate to sanitizing a surface target area, meaning that the area is exposed to a dosage of light calculated to remove unwanted compounds without fully sterilizing the surface, e.g., about 25% to about 98%; artisans will immediately appreciate that all the ranges and values within the explicitly stated ranges are contemplated, e.g., from about 50% to about 80%. Certain embodiments of sanitization/ sterilization are directed to one or more combinations of organisms or conditions and/or specific items and/or areas and/or area sizes and/or light source devices as in Table 1. The devices of Table 1 have been made and tested as prototypes or designed as indicated. Disinfecting is a term applied to either sanitization or sterilization.

The sterilization/sanitization devices may provide users with options to control settings or choose conditions the user wishes to address. For instance, an interactive display or a selection device (e.g., switch, knob, slider) may allow a user to select for one or more conditions as in Table 1, e.g., mold A so that the device is instructed to require a predetermined dosage value of 10,000 microwatts per cm2 for sterilization.

In some embodiments, a user is allowed to select a sanitization setting for less than complete sterilization, or to select an overexposure setting. Alternatively, overexposure may be built into the device's processing routines to provide a safety margin.

Patents, patent applications, and publications set forth herein are hereby incorporated by reference herein to the extent they do not contradict what is explicitly disclosed herein. The embodiments describe a variety of features. In general, the features may be mixed-and-matched to make other embodiments as guided by the need to make a functional device.

TABLE 1

| Model Reference No. | | 1 | 2 | 6 | 7 | 10 | 20 |
|---|---|---|---|---|---|---|---|
| Type Device | | Wand | Wand | Wand | Flip Wand | Rollable | Rollable Vacuum |
| Output UVC | Watts | 6 | 3 | 8 | 1.5 | 4 | 35 |
| Intensity UVC | μW/cm2 | 4750 | 1710 | 5000 | 4950 | 1000 | 21875 |
| Total Output of Light Source | μW/Ttl. area | 213750 | 25650 | 312500 | 29700 | 38000 | 1312500 |

Organism or Condition: Typhoid. Required Dosage to kill organism: 6000 μWs/cm2

| AREA, cm2 | DIMENSION | ITEM | Minutes for 99.9% Kill Rate | | | | | |
|---|---|---|---|---|---|---|---|---|
| 1 | (1 cm × 1 cm) | 1 Square cm | 0.02 | 0.06 | 0.02 | 0.02 | 0.10 | 0.00 |
| 72 | (18 cm × 4 cm) | Remote Control | 0.03 | 0.28 | 0.02 | 0.24 | 0.19 | 0.01 |
| 144 | (18 cm × 4 c × 2) | Telephone | 0.07 | 0.56 | 0.05 | 0.48 | 0.38 | 0.01 |
| 480 | (40 cm × 32 cm) | Toilet Seat | 0.22 | 1.87 | 0.15 | 1.62 | 1.26 | 0.04 |
| 2394 | (63 cm × 38 cm) | Queen Pillow | 1.12 | 9.33 | 0.77 | 8.06 | 6.30 | 0.18 |
| 9677 | (127 cm × 76 cm) | Baby Crib Matress | 4.53 | 37.73 | 3.10 | 32.58 | 25.47 | 0.74 |
| 18909 | (191 cm × 99 cm) | Single Matress | 8.85 | 73.72 | 6.05 | 63.67 | 49.76 | 1.44 |
| 26167 | (191 cm × 137 cm) | Double Matress | 12.24 | 102.02 | 8.37 | 88.10 | 68.86 | 1.99 |
| 30856 | (203 cm × 152 cm) | Queen Matress | 14.44 | 120.30 | 9.87 | 103.89 | 81.20 | 2.35 |
| 39179 | (203 cm × 193 cm) | King Matress | 18.33 | 152.74 | 12.54 | 131.92 | 103.10 | 2.99 |

Organism or Condition: Influenza. Required Dosage to kill organism: 6,600 μWs/cm2

| AREA, cm2 | DIMENSION | ITEM | Minutes for 99.9% Kill Rate | | | | | |
|---|---|---|---|---|---|---|---|---|
| 1 | (1 cm × 1 cm) | 1 Square cm | 0.02 | 0.06 | 0.02 | 0.02 | 0.11 | 0.01 |
| 72 | (18 cm × 4 cm) | Remote Control | 0.04 | 0.31 | 0.03 | 0.27 | 0.21 | 0.01 |
| 144 | (18 cm × 4 c × 2) | Telephone | 0.07 | 0.62 | 0.05 | 0.53 | 0.42 | 0.01 |
| 480 | (40 cm × 32 cm) | Toilet Seat | 0.25 | 2.06 | 0.17 | 1.78 | 1.39 | 0.04 |
| 2394 | (63 cm × 38 cm) | Queen Pillow | 1.23 | 10.27 | 0.84 | 8.87 | 6.93 | 0.20 |
| 9677 | (127 cm × 76 cm) | Baby Crib Matress | 4.98 | 41.50 | 3.41 | 35.84 | 28.01 | 0.81 |
| 18909 | (191 cm × 99 cm) | Single Matress | 9.73 | 81.09 | 6.66 | 70.03 | 54.74 | 1.58 |
| 26167 | (191 cm × 137 cm) | Double Matress | 13.47 | 112.22 | 9.21 | 96.91 | 75.75 | 2.19 |
| 30856 | (203 cm × 152 cm) | Queen Matress | 15.88 | 132.33 | 10.86 | 114.28 | 89.32 | 2.59 |
| 39179 | (203 cm × 193 cm) | King Matress | 20.16 | 168.02 | 13.79 | 145.11 | 113.41 | 3.28 |

Organism or Condition: Hepatitis. Required Dosage to kill organism: 8,000 μWs/cm2

| AREA, cm2 | DIMENSION | ITEM | Minutes for 99.9% Kill Rate | | | | | |
|---|---|---|---|---|---|---|---|---|
| 1 | (1 cm × 1 cm) | 1 Square cm | 0.03 | 0.06 | 0.02 | 0.02 | 0.11 | 0.01 |
| 72 | (18 cm × 4 cm) | Remote Control | 0.04 | 0.37 | 0.03 | 0.32 | 0.25 | 0.01 |
| 144 | (18 cm × 4 c × 2) | Telephone | 0.09 | 0.75 | 0.06 | 0.65 | 0.51 | 0.01 |
| 480 | (40 cm × 32 cm) | Toilet Seat | 0.30 | 2.50 | 0.20 | 2.15 | 1.68 | 0.05 |
| 2394 | (63 cm × 38 cm) | Queen Pillow | 1.49 | 12.44 | 1.02 | 10.75 | 8.40 | 0.24 |
| 9677 | (127 cm × 76 cm) | Baby Crib Matress | 6.04 | 50.30 | 4.13 | 43.44 | 33.95 | 0.98 |

TABLE 1-continued

| AREA, cm2 | DIMENSION | ITEM | Minutes for 99.9% Kill Rate | | | | | |
|---|---|---|---|---|---|---|---|---|
| 18909 | (191 cm × 99 cm) | Single Matress | 11.80 | 98.29 | 8.07 | 84.89 | 66.35 | 1.92 |
| 26167 | (191 cm × 137 cm) | Double Matress | 16.32 | 136.02 | 11.16 | 117.47 | 91.81 | 2.66 |
| 30856 | (203 cm × 152 cm) | Queen Matress | 19.25 | 160.40 | 13.17 | 138.52 | 108.27 | 3.13 |
| 39179 | (203 cm × 193 cm) | King Matress | 24.44 | 203.66 | 16.72 | 175.89 | 137.47 | 3.98 |
| Organism or Condition: Anthrax. Required Dosage to kill organism: 8, 8,700 μWs/cm2 | | | | | | | | |
| AREA, cm2 | DIMENSION | ITEM | Minutes for 99.9% Kill Rate | | | | | |
| 1 | (1 cm × 1 cm) | 1 Square cm | 0.03 | 0.08 | 0.03 | 0.03 | 0.15 | 0.01 |
| 72 | (18 cm × 4 cm) | Remote Control | 0.05 | 0.41 | 0.03 | 0.35 | 0.27 | 0.01 |
| 144 | (18 cm × 4 c × 2) | Telephone | 0.10 | 0.81 | 0.07 | 0.70 | 0.55 | 0.02 |
| 480 | (40 cm × 32 cm) | Toilet Seat | 0.33 | 2.71 | 0.22 | 2.34 | 1.83 | 0.05 |
| 2394 | (63 cm × 38 cm) | Queen Pillow | 1.62 | 13.53 | 1.11 | 11.69 | 9.14 | 0.26 |
| 9677 | (127 cm × 76 cm) | Baby Crib Matress | 6.56 | 54.70 | 4.49 | 47.24 | 36.93 | 1.07 |
| 18909 | (191 cm × 99 cm) | Single Matress | 12.83 | 106.89 | 8.77 | 92.32 | 72.15 | 2.09 |
| 26167 | (191 cm × 137 cm) | Double Matress | 17.75 | 147.92 | 12.14 | 127.75 | 99.85 | 2.89 |
| 30856 | (203 cm × 152 cm) | Queen Matress | 20.93 | 174.43 | 14.32 | 150.64 | 117.74 | 3.41 |
| 39179 | (203 cm × 193 cm) | King Matress | 26.58 | 221.48 | 18.18 | 191.28 | 149.50 | 4.33 |
| Organism or Condition: Mold A. Required Dosage to kill organism: 10,000 μWs/cm2 | | | | | | | | |
| AREA, cm2 | DIMENSION | ITEM | Minutes for 99.9% Kill Rate | | | | | |
| 1 | (1 cm × 1 cm) | 1 Square cm | 0.04 | 0.10 | 0.03 | 0.03 | 0.17 | 0.01 |
| 72 | (18 cm × 4 cm) | Remote Control | 0.06 | 0.47 | 0.04 | 0.40 | 0.32 | 0.01 |
| 144 | (18 cm × 4 c × 2) | Telephone | 0.11 | 0.94 | 0.08 | 0.81 | 0.63 | 0.02 |
| 480 | (40 cm × 32 cm) | Toilet Seat | 0.37 | 3.12 | 0.26 | 2.69 | 2.11 | 0.06 |
| 2394 | (63 cm × 38 cm) | Queen Pillow | 1.87 | 15.56 | 1.28 | 13.43 | 10.50 | 0.30 |
| 9677 | (127 cm × 76 cm) | Baby Crib Matress | 7.55 | 62.88 | 5.16 | 54.30 | 42.44 | 1.23 |
| 18909 | (191 cm × 99 cm) | Single Matress | 14.74 | 122.87 | 10.08 | 106.11 | 82.93 | 2.40 |
| 26167 | (191 cm × 137 cm) | Double Matress | 20.40 | 170.03 | 13.96 | 146.84 | 114.77 | 3.32 |
| 30856 | (203 cm × 152 cm) | Queen Matress | 24.06 | 200.49 | 16.46 | 173.15 | 135.33 | 3.92 |
| 39179 | (203 cm × 193 cm) | King Matress | 30.55 | 254.57 | 20.90 | 219.86 | 171.84 | 4.98 |
| Organism or Condition: Mold B. Required Dosage to kill organism: 44,000 μWs/cm2 | | | | | | | | |
| AREA, cm2 | DIMENSION | ITEM | Minutes for 99.9% Kill Rate | | | | | |
| 1 | (1 cm × 1 cm) | 1 Square cm | 0.15 | 0.43 | 0.15 | 0.15 | 0.73 | 0.03 |
| 72 | (18 cm × 4 cm) | Remote Control | 0.25 | 2.06 | 0.17 | 1.78 | 1.39 | 0.04 |
| 144 | (18 cm × 4 c × 2) | Telephone | 0.49 | 4.12 | 0.34 | 3.56 | 2.78 | 0.08 |
| 480 | (40 cm × 32 cm) | Toilet Seat | 1.65 | 13.72 | 1.13 | 11.85 | 9.26 | 0.27 |
| 2394 | (63 cm × 38 cm) | Queen Pillow | 8.21 | 68.44 | 5.62 | 59.11 | 46.20 | 1.34 |
| 9677 | (127 cm × 76 cm) | Baby Crib Matress | 33.20 | 276.67 | 22.71 | 238.94 | 186.75 | 5.41 |
| 18909 | (191 cm × 99 cm) | Single Matress | 64.87 | 540.61 | 44.37 | 466.89 | 364.91 | 10.57 |
| 26167 | (191 cm × 137 cm) | Double Matress | 89.77 | 748.11 | 61.41 | 646.10 | 504.98 | 14.62 |
| 30856 | (203 cm × 152 cm) | Queen Matress | 105.86 | 882.17 | 72.41 | 761.88 | 595.47 | 17.24 |
| 39179 | (203 cm × 193 cm) | King Matress | 134.42 | 1120.13 | 91.94 | 967.38 | 756.09 | 21.89 |

The invention claimed is:

1. A mobile device that provides ultraviolet light for sanitizing or sterilizing a target surface that comprises:
   an ultraviolet light source, a distance detector that measures a distance from the device to the target surface, an indicator, and a microprocessor that receives the distance from the distance detector,
   with the microprocessor comprising programming to
      calculate an intensity of the light from the source on a target surface, with the calculated intensity on the surface used for calculating a dosage of the light on the target surface, and
      to compare the calculated dosage to a predetermined dosage to provide a signal to the indicator when the predetermined dosage is achieved.

2. The device of claim 1 further comprising a movement sensor that provides device movement data to the microprocessor to include in the calculation of the dosage.

3. The device of claim 2 wherein the movement sensor comprises a gyroscope.

4. The device of claim 1 being hand-held and movable over the surface by a user grasping a proximate portion of the device.

5. The device of claim 1 further comprising a wheel for rolling the device across the surface.

6. The device of claim 1 wherein the indicator comprises a light or an audio signal.

7. The device of claim 1 wherein the indicator comprises a display that depicts a subarea of the target surface and the dosage applied to the subarea.

8. The device of claim 2 wherein the movement sensor comprises an accelerometer that provides acceleration data to the microprocessor to be incorporated into the calculation of the dosage.

9. The device of claim 2 wherein the movement sensor provides an acceleration in an x-direction and an acceleration in a y-direction, with the target surface having xy coordinates.

10. The device of claim 1 wherein the microprocessor is programmed to calculate the intensity of the light source at the surface based on a predetermined value of intensity of the light source at the light source and the distance from the light source to the surface as measured by the distance detector.

11. The device of claim 1 wherein the target surface is represented as having an x-direction and a y-direction, with the calculations subdividing the surface into a plurality of grid members and calculating a dosage for each grid member.

12. The device of claim 11 wherein a display provides a visual representation of a dosage received at each grid member.

13. The device of claim 1 further comprising executable instructions in computer readable medium for comparing the dosage to predetermined sterilization dosages for one or more organisms or conditions in the group consisting of typhoid, influenza, hepatitis, anthrax, mold A, and mold B.

14. The device of claim 1 further comprising executable instructions in computer readable medium for comparing the dosage to predetermined dosages from about 5,000 to about 100,000 microwatt-seconds per square centimeter.

15. The device of claim 1 configured as a hand-held wand with a light source disposable in an extended position for sterilization and a retracted storage position wherein the light source is stored internally to the device.

16. The device of claim 15 comprising a pivotable member to move the device from the extended position to the storage position, with the pivotable member being biased to reversibly lock the device in the extended position.

17. The device of claim 1 wherein the UV light source is a UVA light source, a UVB light source, a UVC light source or a combination UVA and UVB and UVC light source.

18. A method of disinfecting comprising moving the device of claim 1 to expose a target area to the light source until the indicator indicates the predetermined dosage is achieved.

19. The method of claim 18 wherein the indicator comprises a display that depicts subareas of the target area and the dosage applied to the subareas, wherein the user moves the device over the subareas until each subarea has achieved the predetermined dosage.

20. The method of claim 18 wherein the device further comprises a movement sensor that comprises an accelerometer that provides acceleration data to the microprocessor to be incorporated into the calculation of the dosage.

21. The method of claim 20 wherein the movement sensor provides an acceleration in an x-direction and an acceleration in a y-direction, with the target area having xy coordinates.

22. The method of claim 20 wherein the target area is represented as having an x-direction and a y-direction, with the calculations subdividing the area into subareas and calculating a dosage for each subarea.

23. A method of making a mobile disinfecting device for sanitizing or sterilizing a surface comprising mounting an ultraviolet light source in a housing in electronic communication with a microprocessor that communicates with a movement sensor and a distance detector that measures a distance between the device and the surface, wherein the movement sensor is configured to provide movement information to the microprocessor, with the microprocessor comprising programming for
   using the distance to calculate an intensity of the light source at the surface,
   calculation of a dosage at the surface based on the intensity of the light source at the surface,
   comparison of the dosage to a predetermined dosage, and
   activation of an indicator when the dosage at the surface achieves the predetermined dosage.

24. The method of claim 23 further comprising programming for predetermined sterilization dosages for one or more organisms or conditions in the group consisting of typhoid, influenza, hepatitis, anthrax, mold A, and mold B.

25. The method of claim 23, wherein the device is hand-held and movable over the surface by a user grasping a proximate portion of the device.

26. The method of claim 23, with the device further comprising a wheel for rolling the device across the surface.

27. The method of claim 23, wherein the movement sensor provides an acceleration in an x-direction and an acceleration in a y-direction, with the surface having xy coordinates.

28. The method of claim 23, wherein the microprocessor is configured to calculate the dosage with an intensity of the light source at the surface, a predetermined value of intensity of the light source at the light source, and a distance from the light source to the surface.

29. The method of claim 23, with the device further comprising executable instructions in computer readable medium for comparing the dosage to predetermined dosages from about 5,000 to about 100,000 microwatt seconds per square centimeter.

30. The device of claim 3 configured as a hand-held wand.

31. The device of claim 3 configured as a vacuum-cleaner.

* * * * *